(12) United States Patent
Kloos et al.

(10) Patent No.: US 7,862,621 B2
(45) Date of Patent: Jan. 4, 2011

(54) PROSTHESIS, IN PARTICULAR PROSTHETIC FOOT

(75) Inventors: Ralf Kloos, Heroldstatt (DE); Armin Grab, Leinfelden-Echterdingen (DE); Julia Grunwald, Berlin (DE); Urs Schneider, Stuttgart (DE); Kai Von Lübtow, Stuttgart (DE)

(73) Assignee: Fraunhofer-Gesellschaft zur Forderung der Angewandten Forschung E.V., Munich (DE)

( * ) Notice: Subject to any disclaimer, the term of this patent is extended or adjusted under 35 U.S.C. 154(b) by 601 days.

(21) Appl. No.: 11/659,169

(22) PCT Filed: Aug. 3, 2005

(86) PCT No.: PCT/EP2005/008420
§ 371 (c)(1),
(2), (4) Date: Mar. 21, 2007

(87) PCT Pub. No.: WO2006/015787
PCT Pub. Date: Feb. 16, 2006

(65) Prior Publication Data
US 2007/0255427 A1    Nov. 1, 2007

(30) Foreign Application Priority Data
Aug. 4, 2004    (DE)    ........................ 10 2004 037 877

(51) Int. Cl.
A61F 2/66    (2006.01)
A61F 2/68    (2006.01)
(52) U.S. Cl. .......................................... 623/49; 623/53
(58) Field of Classification Search .............. 623/47–55
See application file for complete search history.

(56) References Cited

U.S. PATENT DOCUMENTS 2,073,807 A    3/1937    Ronowsky
(Continued)

FOREIGN PATENT DOCUMENTS

AT    16 22 41    2/1949
(Continued)

OTHER PUBLICATIONS

Macmillan Online Dictionary, Dictionary Definition of Term "Resilient"; accessed Jul. 1, 2010.*

Primary Examiner—William H Matthews
Assistant Examiner—Marcia Hoffman
(74) Attorney, Agent, or Firm—Fulbright & Jaworski L.L.P.

(57)    ABSTRACT

The invention relates to a prosthetic device (30), in particular a foot prosthesis, for fitting leg amputees, with a universal joint mechanism (32), which couples a shaft (34) with a treading attachment (40, 42) through an articulation, wherein the universal joint mechanism (32) comprises a joint element (44) supported such that it is rotatable about a first rotational axis (C) and a second rotational axis (D) differing therefrom. For more accurate modeling of the natural gait of a healthy human foot, the invention provides that the universal joint mechanism (32) comprises a shaft-side joint fork (36) coupleable with the shaft (34) and a treading-side joint fork (38) coupled via the joint element (44) through an articulation with the shaft-side joint fork (36), wherein the shaft-side joint fork (36) is swivellable about the first rotational axis (C) and the treading-side joint fork (38) about the second rotational axis (D) relative to the joint element (44), and wherein the swivel movements of shaft-side and treading-side joint fork (36, 38) relative to the joint element (44) are carried out against the resistance of at least one damping element (90, 92) proximal to the joint element.

2 Claims, 8 Drawing Sheets

U.S. PATENT DOCUMENTS

| | | |
|---|---|---|
| 2,644,165 A | 7/1953 | Grisoni |
| 2,692,990 A | 11/1954 | Schaefer |
| 4,328,594 A | 5/1982 | Campbell et al. |
| 4,645,509 A | 2/1987 | Poggi et al. |
| 4,822,363 A | 4/1989 | Phillips |
| 4,892,554 A | 1/1990 | Robinson |
| 4,932,806 A | 6/1990 | Eklund et al. |
| 5,019,109 A * | 5/1991 | Voisin .................. 623/49 |
| 5,116,385 A | 5/1992 | Allard et al. |
| 5,181,933 A | 1/1993 | Phillips |
| 5,219,365 A | 6/1993 | Sabolich |
| 5,314,499 A | 5/1994 | Collier, Jr. |
| 5,425,780 A | 6/1995 | Flatt et al. |
| 5,482,513 A * | 1/1996 | Wilson .................. 623/52 |
| 5,800,570 A | 9/1998 | Collier |
| 6,129,766 A * | 10/2000 | Johnson et al. .......... 623/49 |
| 6,743,260 B2 * | 6/2004 | Townsend et al. ........ 623/52 |
| 7,112,227 B2 * | 9/2006 | Doddroe et al. .......... 623/49 |
| 2003/0105531 A1 | 6/2003 | Bunn |

FOREIGN PATENT DOCUMENTS

| | | |
|---|---|---|
| DE | 807 114 | 7/1949 |
| DE | 818 677 | 7/1949 |
| DE | 846 891 | 7/1949 |
| DE | 804 830 | 4/1951 |
| DE | 17 01 723 | 6/1955 |
| DE | 42 08 941 C2 | 9/1993 |
| DE | 298 20 904.7 | 11/1998 |
| EP | 0 498 586 A1 | 8/1992 |
| EP | 1 128 789 B1 | 9/2001 |
| WO | WO-94/22399 | 10/1994 |
| WO | WO-96/23461 | 8/1996 |

* cited by examiner

PROSTHESIS, IN PARTICULAR PROSTHETIC FOOT

This is a §371 of PCT/EP2005/008420 filed Aug. 3, 2005, which claims priority from German Patent Application No. 10 2004 037 877.0 filed Aug. 4, 2004.

BACKGROUND OF THE INVENTION

The present invention relates to a prosthesis, in particular a foot prosthesis, for the fitting of leg amputees, according to the preamble of patent claim 1.

The biomechanical processes of human walking are composed of a plurality of movements of individual body parts. In the course thereof extremely complex processes are taking place in the region of the lower extremities. Here various joints cooperate synchronously and synergistically in order to cushion the reaction forces occurring at the point of origin, which means the treading plantar-Surface of the foot, in order to conduct propelling forces efficiently into the ground and to compensate potential unevennesses on the ground such that the rest of the body does not need to perform energy consuming compensatory movements. The joints in the foot assume therein great significance in particular the upper ankle joint (OSG) and the lower ankle joint (USG). Each of the two ankle joints located in the proximity of the malleolus of a human foot has a rotational axis with a specific orientation with respect to the other. FIG. 12a to 12h show the progression of the rotational axis A of the upper ankle joint and of the rotational axis B of the lower ankle joint relative to the human foot. For simplification of the explanation, here a spatial system of coordinates with the axes X, Y and Z is introduced, where the X-Y plane is defined by the fixed points 10, 12 and 14 of the human foot and the direction of the X-axis by its longitudinal extent, wherein further the Y-axis is always directed toward the outside of the foot and the Z-axis is orthogonal to axis X, and Y extends substantially in the longitudinal direction of the lower leg in the relaxed resting position of the foot 16.

Figure 12A:
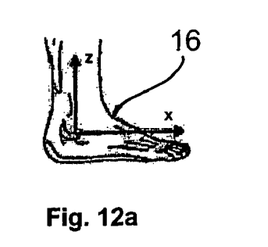
Figure 12B:
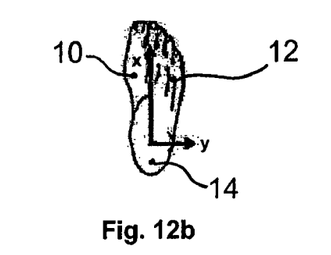
Figure 12C:
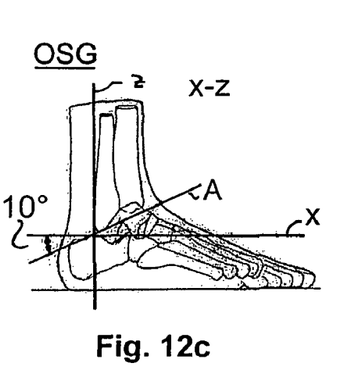
Figure 12D:
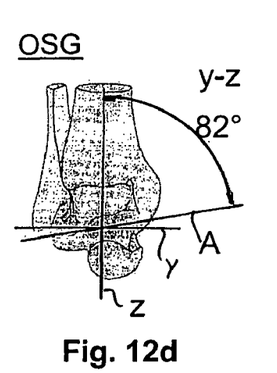
Figure 12E:
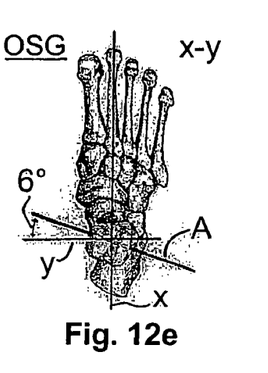
Figure 12F:
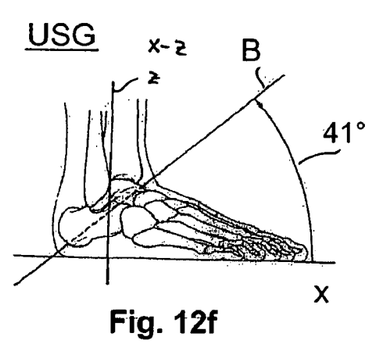
Figure 12G:
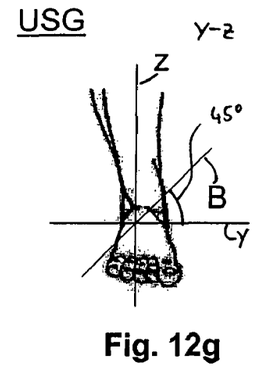
Figure 12H:
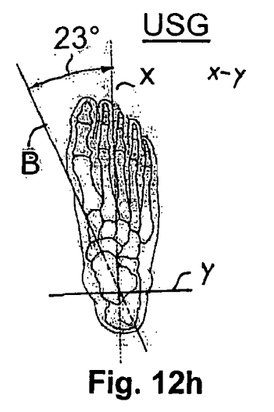
Figure 13A:
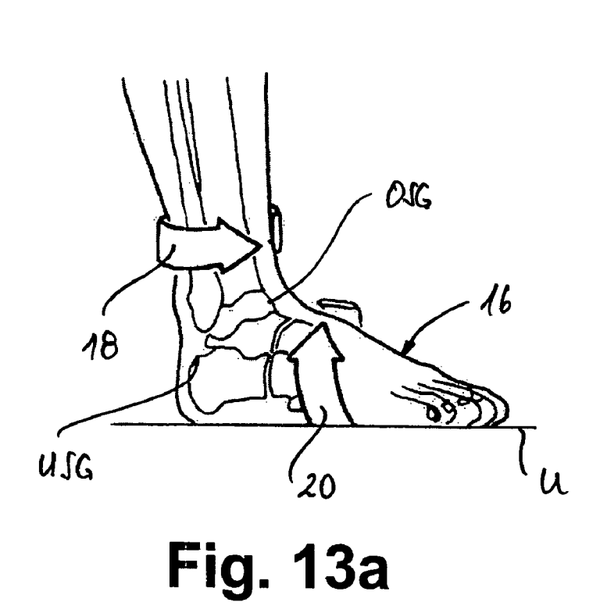
Figure 13B:
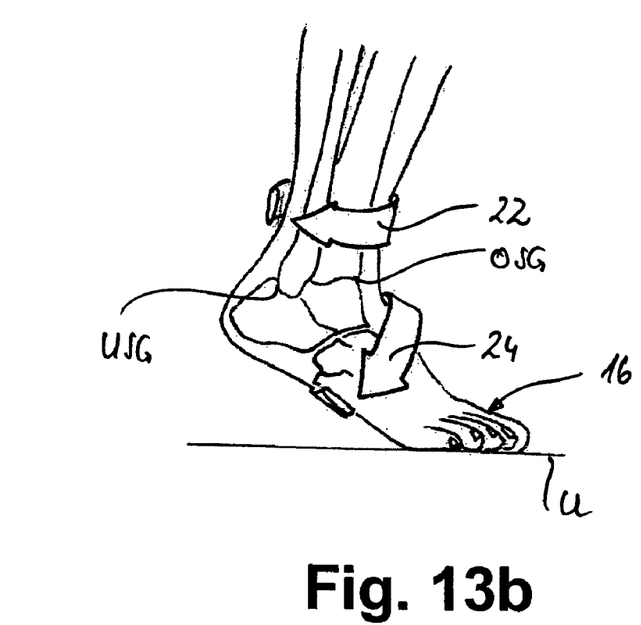

If such a system of coordinates is assumed, it can be seen that the rotational axis A of the upper ankle joint is inclined in the X-Z plane according to FIG. 12c substantially at 10° relative to the X-axis, in the X-Y plane according to FIG. 12c substantially at 82° relative to the Z-axis and in the X-Y plane according to FIG. 12e substantially at 6° with respect to the Y-axis. It can further be seen that the rotational axis B of the lower ankle joint is inclined in the X-Z plane according to FIG. 12f substantially at 41° with respect to a line parallel to the X-axis, in the Y-Z plane according to FIG. 12g substantially at 45° with respect to the Y-axis and in the X-Y plane according to FIG. 12h substantially at 23° with respect to the X-axis. These progressions of the rotational axes of the upper ankle joint OSG and of the lower ankle joint USG in a normal gait pattern of a healthy human foot lead to specific movement sequences, in particular to relative movements between lower leg and foot. For an explanation of these movement sequences reference is made to FIG. 13a and 13b. FIG. 13a shows the movements when the foot 16 is placed on a ground U up to the middle stance phase. FIG. 13b shows the further movement sequence when the foot 16 is rolled over the ball of the foot.

When placing the foot according to FIG. 13a an inner rotation of the lower leg according to arrow 18 occurs due to a rotation of the hip and to a simultaneous eversion (outward rotation) of the foot according to arrow 20, until the middle stance phase according to FIG. 13a has been reached. In the succeeding roll-off and push-off according to FIG. 13b, in contrast, an outer rotation of the lower leg occurs according to arrow 22 and, on the other hand, an inversion of the foot takes place synchronously, according to arrow 24. These cooperating movements according to FIG. 13a and 13b in the proximity of the upper and lower ankle joint of the human foot are decisive for the efficient cushioning of ground reaction forces and a restrained transfer of the rotation of the human hip to the ground, and conversely, during human walking, such that the movement apparatus can be utilized efficiently and with restraint.

The challenge has existed for a long time in the field of prosthetics to simulate the complicated biomechanical processes in the lower extremities as exactly as possible in a prosthetic device in order to be able offer patients whose legs had been amputated prosthetic devices which permit mimicking the complex human gait as authentically as possible. For this purpose it is necessary to provide the individual prosthetic devices with joints, which, on the one hand, ensure sufficient stabilization for the legless person, however, on the other hand, have such flexibility that they make possible the unimpeded locomotion of a person. An essential aspect is herein that the gait pattern achieved is as economic as possible, in order to keep the efforts in the forward progression of the legless person low. It must be taken into consideration that leg amputees are often patients with at least a restricted degree of mobility, whose training status is weakly developed so that additional efforts caused by the dynamic behavior of the prosthetic device could further restrict the degree of mobility. It must moreover be taken into consideration that with a nonsymmetric gait pattern, due to the dynamic behavior of the prosthetic device, damage to the vertebral spine, in particular the lumbar portion of the spine, may occur. A nonsymmetric gait pattern due to a prosthesis can moreover lead to unusually strong stress or even to wear phenomena on the healthy leg as well as on the still functioning knee joint ligament of the amputated leg. In addition to the disablement due to the amputation, hip damage, damage to the intervertebral disks, joint instabilities or even arthrosis may develop as a consequence of such unnatural stresses.

Attempts have therefore been undertaken in prior art to provide through various measures prosthetic devices which at least approximately exhibit similar dynamic behavior as a natural human foot during normal human walking.

U.S. Pat. No. 5,425,780 discloses a lower leg prosthesis of the above described type, in which via a universal [Cardan] joint a foot section is connected with a lower leg shaft. The device shown here is structured in such a way that it is relatively complicated and requires much space, which is of disadvantage in particular in view of its weight and wearing comfort. Moreover, this prior art prosthesis exhibits dynamic behavior which strongly differs from the natural dynamic behavior of a human foot, since the orientation of the universal [Cardan] axes deviate significantly from the orientation of the biomechanical axes of the upper and the lower ankle joint.

WO 94/22399 describes a foot prosthesis which is also provided with a universal joint. The universal joint in this foot prosthesis is formed by a pivot pin as well as a pivot bearing rotationally receiving the bearing pin orthogonal to its longitudinal extent. While thereby a movement of the foot prosthesis about two axes relative to the shaft can be realized, however, the axes, again, are oriented significantly discrepant from the biomechanical axes of the upper and lower ankle joint. The axis position, moreover, also deviates markedly from the axis position of the upper and lower ankle joint. The two rotational axes are not located in a region proximal to the treading attachment, but rather markedly above the treading attachment, that means at a site at which no rotational movement takes place in a natural human foot. This foot prosthesis also leads to an unnatural gait pattern and to the above described disadvantages for the patient with respect to excessive loading. The same disadvantages are entailed in the foot prostheses known from documents AT 16 22 41, U.S. Pat. No. 2,692,990, U.S. Pat. No. 2,644,165 and DE 804 830.

As further prior art is cited U.S. Pat. No. 5,314,499. This prior art provides a foot prosthesis with a single pivot joint to connect the shaft with the treading attachment. The above described corresponding relative rotational movements during the process of natural walking cannot be mimicked with Such a one-axis joint.

For technical background of the present invention reference is further made to prior art according to EP 1 128 789 B1, U.S. Pat. No. 5,800,570, U.S. Pat. No. 4,892,554 and EP 0 498 586.

Further, a foot prosthesis is disclosed in DE 42 08 941 C2, which, in the interest of a mechanically simple structure, attempts to suffice entirely without joint element.

From the category-defining prior art according to DE 818 677 a foot prosthesis is known in which a universal joint mechanism couples a treading body with a shaft. The disposition and the orientation of the universal joint mechanism in this arrangement also differs significantly from the biomechanical axes of the upper and the lower ankle joint, such that the foot prosthesis leads to all unnatural gait pattern and to the above multiply addressed unnatural loading for the patients. There is furthermore a damping element provided, which is disposed about the universal joint mechanism and cooperates with the shaft in order to dampen a relative movement of the shaft relative to the treading body. This disposition of the damping element ensures, for one, a biomechanically unnatural damping behavior of the foot prosthesis and, for another, moreover leads to a structural form requiring relatively large space.

The problem addressed by the present invention, in contrast, is to provide a prosthesis of the above described type in which a compact structure is capable of modeling the biomechanical processes of the natural, i.e. physiological, gait pattern of man in the region of an upper and lower ankle joint and to do so as authentically as is possible.

This problem is solved according to the invention through a prosthesis—in the following also referred to as "prosthetic device"—with the characteristics of patent claim 1.

BRIEF SUMMARY OF THE INVENTION

Through the invented prosthesis, in particular the invented implementation of the universal joint mechanism, an extremely compact modeling of the human foot can be achieved which can be oriented such that the two rotational axes can be disposed in positions which, with respect to one another, are oriented in positions corresponding to the human ankle joint. With the invented foot prosthesis, consequently, a dynamics is attained which models the biomechanical processes during natural walking. Integration of the at least one damping element in a region proximal to the axis between the joint element and one of the joint parts permits furthermore an extremely compact and stable structuring of the invented prosthetic device, the damping action—similar to the human ankle joint—in fact, also occurring close to the rotational axes.

Compared to the above described prior art, overall a markedly simplified and more compact prosthetic device can be attained according to the invention, which device, as will be explained in the following in detail, can be disposed corresponding to the orientation of the rotational axes of the upper and the lower ankle joint of the natural foot and which, during the process of walking, functions largely like a natural human foot. The above defined aim of a natural cushioning of ground reaction forces and transfer of the hip rotation onto the foot with the economic utilization of the still retained movement apparatus of the patient as well as the avoidance of unnatural stresses on the vertebral column, the hip, the other healthy leg or the still remaining shortened leg can thereby be achieved.

A further development of the invention provides that the joint element is implemented in the form of a disk and that the rotational axes penetrate its end face. The structure of the universal joint mechanism is thereby simplified and the proneness to defects reduced.

With respect to the mechanical structure of the universal joint mechanism, it may further be provided that at least one joint part is implemented as a joint fork with two fork jaws encompassing the joint element on opposite sides of its end face. In the manner of a universal joint the two joint parts engage one another with the interposition of the joint element and are supported rotatably about the two rotational axes. For wear reduction and for minimizing undesirable functional effects, a further development of the invention provides supporting the joint element such that it is rotatable relative to the joint parts.

The pivot bearings can be implemented in a manner known per se with rolling bodies. However, an advantageous embodiment of the invention provides that at least one of the pivot bearings is implemented as a friction bearing. With respect to low friction level, the bearing properties of function bearings are sufficient for the present case of a foot prosthesis. By using friction bearings the maintenance expenditure of the invented prosthetic device can be considerably reduced and the stability and service life increased. It is preferably provided that at least to one of the rotational axes is assigned an axially aligned pair of rotational bearings in each of the fork jaws of the particular joint part, implemented as a joint fork, a pivot bearing being disposed. The pivot bearings can be received in the particular fork jaws in receiving openings and be pressed or otherwise secured in them, for example by staying, adhesion or screwing in.

A further development of the invention provides that the joint element is rotatable about one of the rotational axes with at least one of the joint parts via a singular pivot bearing and that a rotational movement about these rotational axes takes place against the resistance of a damping element. In this embodiment the joint part with the singular pivot bearing, deviating from a conventional universal joint shaft or universal joint, is not implemented in the form of a fork but rather is only coupled via the singular pivot bearing with the joint element. In a region remote from the singular pivot bearing the at least one damping element can be provided, which replaces the second pivot bearing. It is understood that a relative movement between joint element and joint part provided with a singular pivot bearing is substantially prevented in the direction of the rotational axis. The compactness of the configuration can be further increased through this embodiment.

With respect to the rotational mobility of joint element and joint parts with respect to one another, a further development of the invention provides that for the pivotable support of the joint element relative to at least one of the joint parts, bearing bolts are provided, wherein in particular each bearing bolt is axially braced on an associated joint part, is rotatably received in the pivot bearing of the particular joint part and is connected torque tight with the joint element. Such a structuring permits simple production and mounting as well as easy maintenance of the inventive prosthetic device. It is understood that other constructional variants are also conceivable, for example such in which the joint parts are divided and the joint element comprises at its end faces projecting bearing pins supported in corresponding bores within the joint parts. In the embodiment preferred according to the invention with bearing bolts a further development of the invention provides that the bearing bolts comprise a bearing head which, by means of a support disk, is braced under low-friction on the joint part associated with it. In this connection it can further be provided that the bearing head and the support disk of at least one of the bearing bolts is at least partially received in a countersinking in the particular joint part. Thereby the invented prosthetic device can be formed even more compactly.

The at least one damping element, already addressed several times above, represents an essential component of the invention. It is in principle possible to cushion or dampen the relative movement of the axes for example by torsion springs or the like. However, this leads to relatively high technical expenditures and, as a rule, is not maintenance friendly. The invention provides that the damping element engages directly on the parts movable with respect to one another, namely the joint part and the joint element. In the natural human foot the particular ligaments and muscles also engage in corresponding manner on the parts movable with respect to one another, such that the prosthetic device according to the invention in this respect also models the biomechanical structure of the natural human foot.

Regarding the compactness of the prosthetic device according to the invention with respect to the disposition of the damping element, a further development of the invention provides that the at least one damping element is received in a receiving opening in one of the joint parts. Thereby spatial fixing of the damping element can additionally be attained. It further prevents that the element slips into a position impairing the function of the invented prosthetic device, for example after long operation times.

In the introduction the position of the rotational axes of the upper and lower ankle joint and the sequence of relative movements during natural walking of a person with respect to a "standard foot" was discussed in conjunction with FIG. 12a to 12h and 13a as well as 13b. However, a person of skill in the art understands that no human pair of feet is identical to another and that in practice there is a plurality of possible discrepant orientations and biomechanical characteristics entirely different from the orientations described. Accordingly, it is advantageous that the prosthetic device of the invented type in a further development can be adapted to the particular individual requirements of the patients to be fitted with the prosthetic device. Fine tuning of the invented prosthetic device is possible for example thereby that the at least one damping element can be displaced via an advancing device, preferably a pressure disk adjustable via threads, relative to the joint part and the joint element, and/or can be advanced toward the joint element.

This permits the prestress of the damping element to be adjusted and thus the prosthetic device to be adapted to the other, still healthy, foot.

A further development of the invention provides that the at least one damping element is formed by an elastically deformable damping body, preferably a hollow cylindrical damping body. It is understood that damping elements of a different type may be employed, for example combined spring damping elements comprising a compression spring, torsion spring, tension spring or the like. Depending on the need for adaptation of the prosthetic device to the patient, the resilient and damping elements may exhibit linear, progressive or degressive resilient and damping characteristics, or a hysteresis behavior.

In the event the above described adaptation by changing the prestress of the damping element via the advancing device does not yield an optimal adaptation result of the invented prosthetic device to the patient to be fitted, the invention further provides that a plurality of damping bodies, each having different hardness and/or different damping behavior, is optionally insertable as a damping element into the prosthetic device. The above addressed damping bodies with highly diverse characteristics can accordingly be exchanged against one another and inserted into the invented prosthetic device in order to provide therewith a multiplicity of adaptation feasibilities.

An advantageous formation of the damping elements with respect to production costs, susceptibility to wear, and therewith service life, is obtained for example if the at least one damping element is produced of an elastomeric synthetic material, preferably of polyurethane.

With respect to the progression of the axes, various configurationl feasibilities also arise. For example, according to one embodiment of the invention it is possible that both rotational axes intersect in the joint element. Alternatively, the two rotational axes may also be skewed with respect to one another. The latter variant corresponds in particular to the progression of the rotational axes of the upper and the lower ankle joint of the natural human foot.

With respect to the cooperation of the at least one damping element with the joint element, a further development of the invention provides that the at least one damping element at least during a deflection of the joint element from a resting position into a position of lateral distance from the intersection or the point of least distance of the rotational axes presses with a force component against the joint element, which [component] extends orthogonally with respect to the two rotational axes. It can thereby be achieved that the invented prosthetic device, in particular the universal joint shaft mechanism provided therein, remains in a resting position and in this resting position, for example during a stance phase or during the middle stance phase of the walking sequence, makes sufficient stability available and Supports the patient. However, as soon as the foot assumes a position which deviates from the position corresponding to the stance phase, for example when treading with the region of the foot prosthesis corresponding to the heel, or when pushing off via the ball of the foot or the region of the foot prosthesis corresponding to the toes, the prosthetic device is deflected out of its resting position such that, independently of the type of deflection, the damping element engages dampingly on the joint element. In this context, the shape of the damping elements is discussed again, which, in the case of a cylindrical or in particular hollow cylindrical implementation, is so disposed that it encompasses in projection said intersection or point of least distance of the rotational axes and, consequently, exerts a damping action on the joint element with any rotational movement of the joint element relative to the joint parts.

One damping element is in principle sufficient to dampen the movements of the joint element relative to the joint parts. To reduce the mechanical loading, and therewith possible wear phenomena, such that overall the service life of the invented prosthetic device can be extended, a further development of the invention provides two or more damping elements, which act from opposite sides onto the joint element.

In the introduction it was explained that through the solution according to the invention an orientation of the rotational axes in the selected universal joint mechanism is possible, which corresponds to the natural progressions of the rotational axes of the upper ankle joint and of the lower ankle joint. In this context a further development provides that in a resting position of the prosthetic device the first rotational axis is inclined in a spatial system of coordinates given by the fixed points of the human foot according to which the orientation of the treading body, referred to in the following also in general as "treading attachment", after application on the treading body-side joint part, is inclined in the plane spanned by the X- and Z-axis at an angle of −10° to 30°, preferably at approximately 10° relative to the X-axis, in the plane spanned by the Y- and Z-axis at an angle of 60° to 100°, preferably at approximately 82° relative to the Z-axis, and in the plane spanned by the X- and Y-axis at an angle of −10° to 20°, preferably at approximately 6° relative to the Y-axis. The system of coordinates is, as explained in the introduction with respect to FIG. 12a to 12h, such that the X- and Y-axes are given by the fixed points of the foot on which the foot in a stance phase is braced on a grounding, wherein the X-axis represents the longitudinal direction of the foot and the Y-axis extends in the plane determined by the fixed points, is orthogonal to the X-axis and is directed toward the outside of the foot. The Z-axis is then orthogonal to the X-axis and to the Y-axis. The common intersection of the axes is such that the Z-axis extends substantially in the longitudinal direction of the lower leg, or, in the case of the prosthesis, in the longitudinal direction of a shaft element. The two systems of coordinates of left and right foot are each mirror-symmetric with respect to the sagittal plane of the body.

In the resting position of the prosthetic device, with such a system of coordinates the invention can further provide that the second rotational axis in a spatial system of coordinates given by the fixed points of the human foot, according to which, after application on the treading body-side joint part, in the following generally denoted by "treading attachment", the orientation of the treading body is determined, is inclined in the plane spanned by the X- and Z-axes at an angle of −15° to 60°, preferably at approximately 41° relative to the X-axis, in the plane spanned by the Y- and Z-axes at an angle of 30° to 60°, preferably at approximately 45° relative to the Y-axis, and in the plane spanned by the X- and Y-axes at an angle of 0° to 40°, preferably at approximately 23° relative to the X-axis.

As already explained above in connection with the adaptability of the invented prosthetic device to the naturally given damping properties of the patient to be fitted, the axis progression of the rotational axes of the upper and lower ankle joint of the patient to be fitted may deviate from the described standard foot. A further development of the invention therefore provides that the orientation of the first rotational axis and/or of the second rotational axis is optionally adjustable. This can be attained for example thereby that different joint parts are made available, each with different progressions of the assigned rotational axes, in the manner of a modular system, which may then be combined with one another depending on requirements. Different joint elements with different axial orientations can further be provided, which, dependent on requirements, can be combined with compatible joint parts. This results in manifold adaptation feasibilities for the adaptation of the invented prosthetic device to the patient to be fitted.

A further development of the invention provides that the treading body is implemented with a foot arch modeled after the human foot arch. In this respect reference is made to EP 1 128 789 B1, which further explains this concept in detail.

With respect to the treading body, it can, moreover, be provided that this body is implemented such that it has damping and/or resilient action. Thereby ground reaction forces can be cushioned or damped near their site of origin, namely in the treading body.

It can further be provided according to the invention that the treading body, preferably via connecting bolts, is fixedly coupleable or is coupled with the treading-side joint part or with a coupling element attached thereto. In this context, the invention can furthermore provide that the treading body is implemented with a heel element and a tread spring.

To couple the invented prosthetic device to a shaft, a further development of the invention provides that the shaft-side joint part is implemented with a shaft adapter, preferably with a pyramid adapter. High wear resistance with simultaneously low weight and low maintenance expenditure is in particular obtained thereby that at least one of the joint parts is produced of metal or synthetic material, in particular of high-grade steel or other mechanically stable materials. It may further be provided in this context that the joint element is produced of metal or synthetic material.

The invention relates further to a universal joint mechanism with the characteristics specific to the universal joint of the above description, in particular a universal joint mechanism for a prosthetic device of the above described type, the universal joint mechanism comprising a first joint part and a second joint part coupled via a joint element in articulation with the first joint part, the first joint part being swivellable about a first rotational axis C and the second joint part about a second rotational axis D relative to the joint element, and the swivel movements of the first and second joint part relative to the joint element being carried out against the resistance of at least one damping element proximal to the joint element. Such universal joint mechanisms can be utilized for different prosthetic devices, however in particular for a foot prosthesis.

BRIEF DESCRIPTION OF THE DRAWINGS

In the following the invention will be explained by example in conjunction with the enclosed Figures. Therein depict.

DETAILED DESCRIPTION OF THE INVENTION

Figure 1:
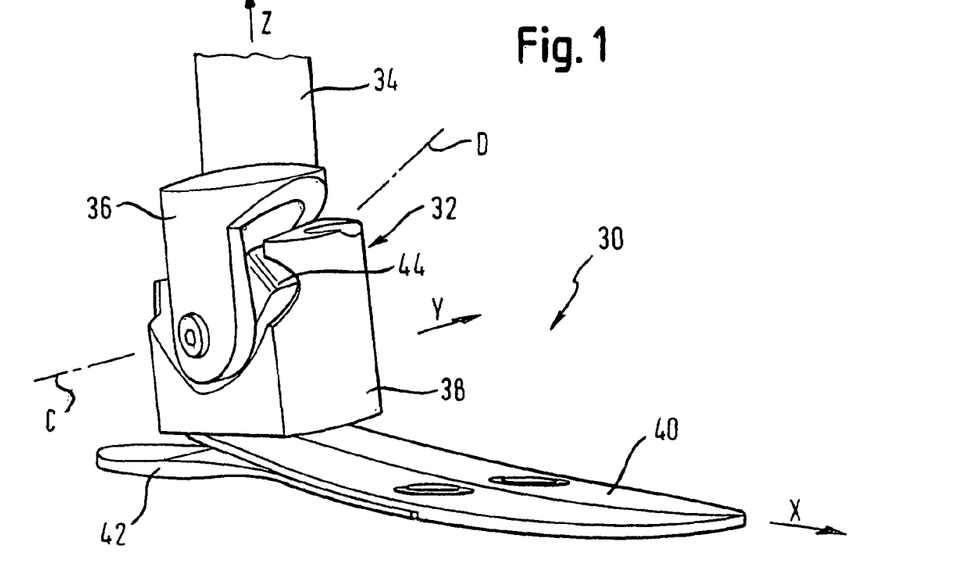
FIG. 1 perspective view of a first embodiment example of an invented prosthetic device with a shaft and a treading attachment, FIG. 2 side view of the universal joint attachment of the invented prosthetic device according to FIG. 1, FIG. 3 view in direction III from FIG. 2 (at a slightly changed scale), FIG. 4 side view in direction IV of FIG. 2 (at a slightly changed scale), FIG. 5 perspective illustration of the universal joint mechanism from FIG. 1, FIG. 6 top view onto the universal joint mechanism in viewing direction VI of FIG. 2, FIG. 7 view from below the invented universal joint mechanism in viewing direction VII of FIG. 2, FIG. 8 sectional view according to section line VIII-VIII of FIG. 6, FIG. 9 sectional view according to section line IX-IX of FIG. 6, FIG. 10 further perspective view of the invented universal joint mechanism of FIG. 1, FIG. 11 semitransparent detail of the invented universal joint mechanism according to FIG. 10, FIG. 12a-12h illustrations of a standard foot to explain the progression of the natural rotational axes of upper and lower ankle joint, FIG. 13a-13b illustrations of a schematic natural human lower extremity to explain movement sequences, FIG. 14 side view of a second embodiment of the invented prosthetic device with treading attachment, FIG. 15 side view of the foot prosthesis mechanism according to FIG. 14, compared to the view of FIG. 14, rotated by 180° about a vertical axis, and FIG. 16 perspective view obliquely from the front of the invented foot prosthesis mechanism according to FIGS. 14 and 15.
Figure 2:
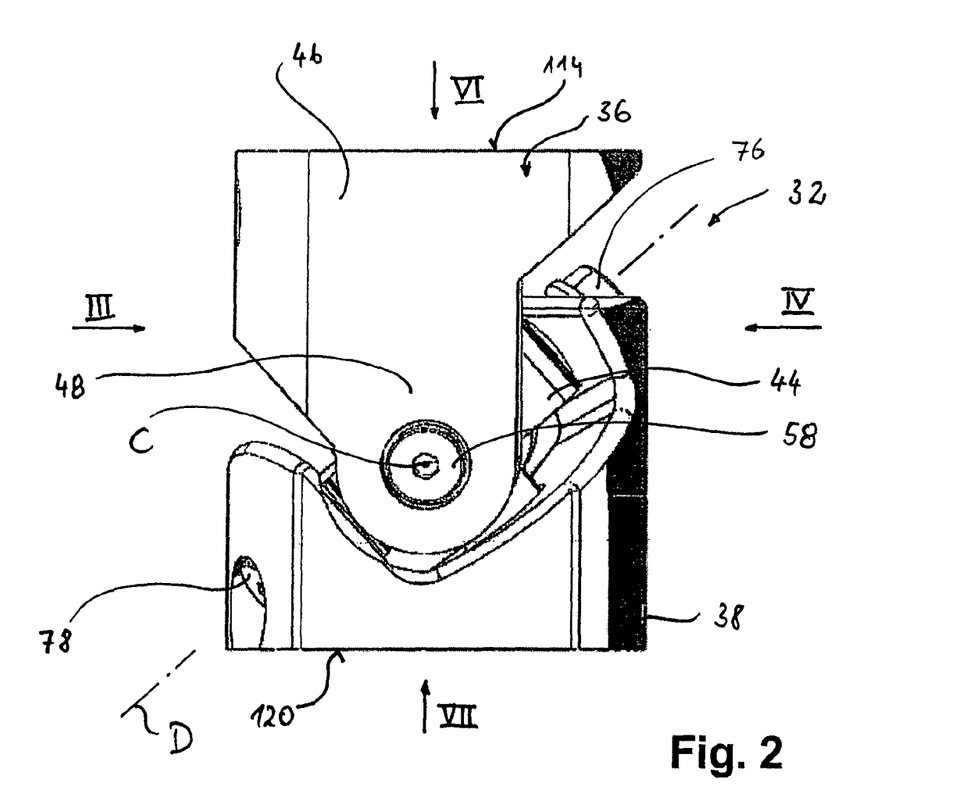
Figure 3:
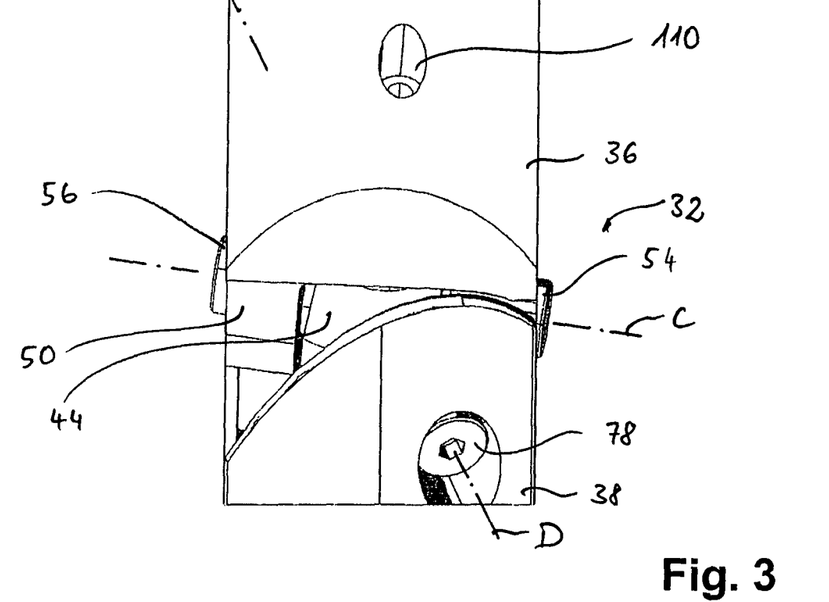
Figure 4:
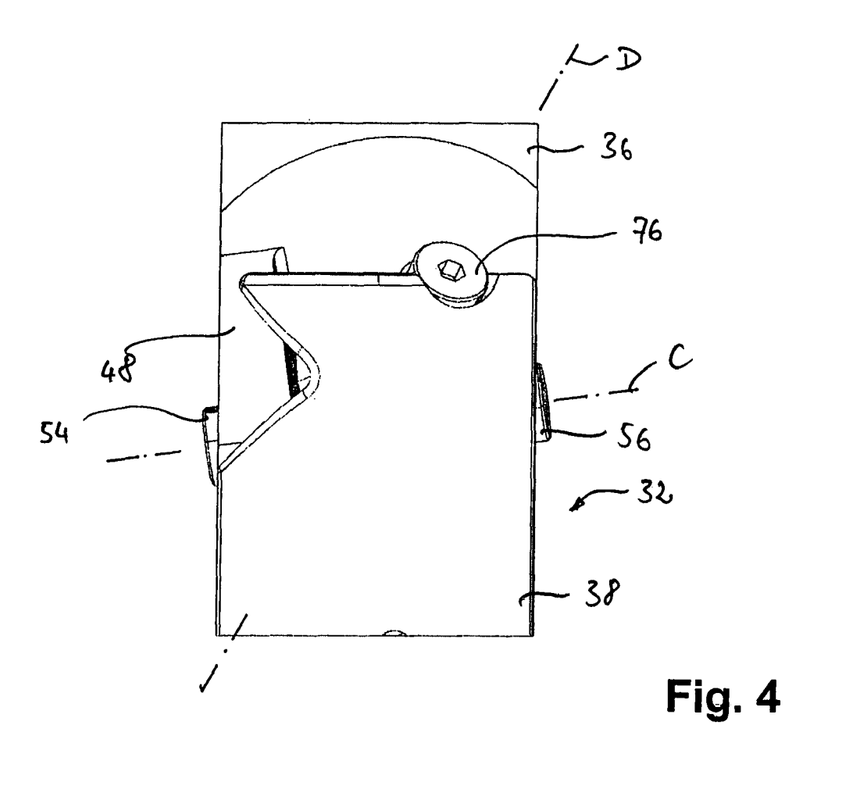
Figure 5:
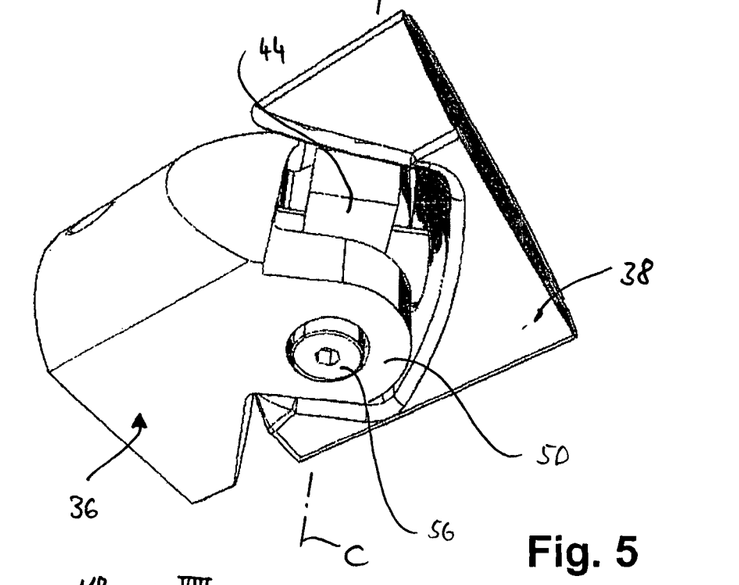

An invented prosthesis device is in FIG. 1 overall denoted by 30.

It comprises a universal joint mechanism 32 coupled with a shaft 34, shown schematically, to a shaft-side joint fork 36. The universal joint mechanism 32 comprises further a treading-side joint fork 38, to which a treading attachment 40 with a heel element 42 is secured. The treading attachment 40 and the heel element 42 are resilient, for example in the form of carbon fiber layers connected with one another.

These two joint parts implemented as joint forks 36 and 38 are rotatably connected with one another via a joint element 44. In particular the shaft-side joint fork 36 is rotatable about a first rotational axis C relative to a joint element 44. The treading-side joint fork 38 is rotatable about a second rotational axis D relative to the joint element 44. Rotational axes C and D of FIG. 1 are only schematically drawn and do not exactly reproduce the progression of these rotational axes proper. This progression is more clearly evident in the following description.

The structure of the invented prosthetic device, in particular of the universal joint mechanism provided therein, will be explained in the following in particular with reference to FIG. 8 and 9, wherein the various views according to FIG. 2 to 7 as well as 10 and 11 will impart to the reader a clear picture of the actual disposition and spatial location of the individual components of the universal joint mechanism 32.

Figure 8:
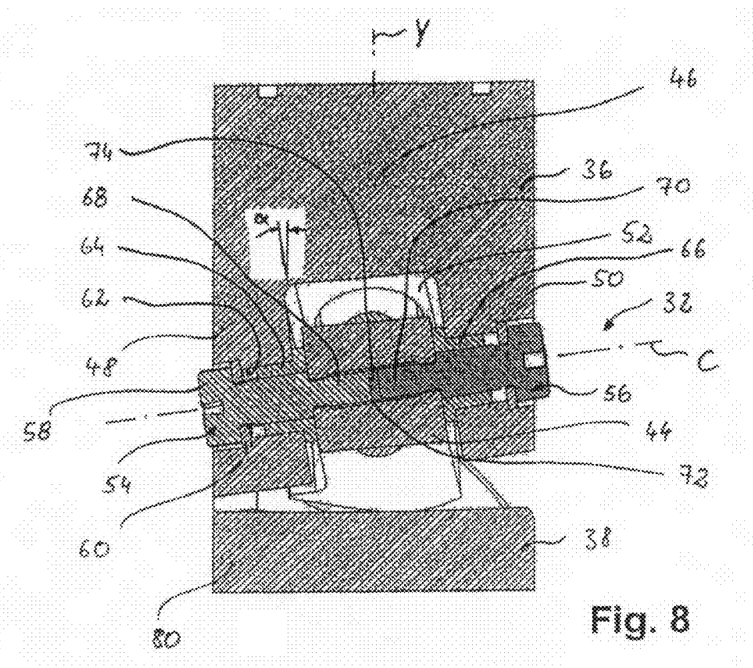
Figure 9:
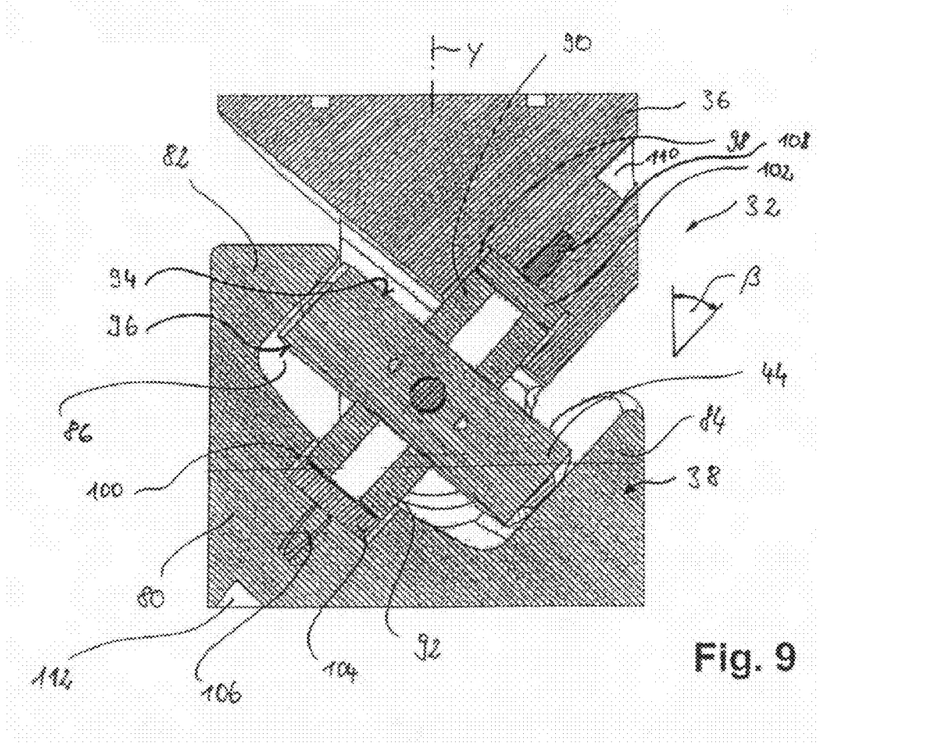
Figure 10:
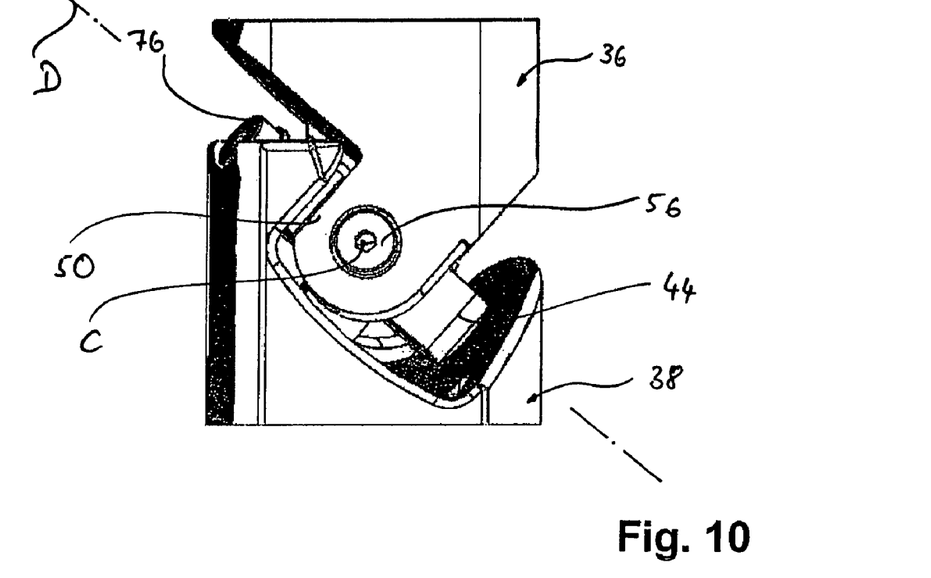
Figure 11:
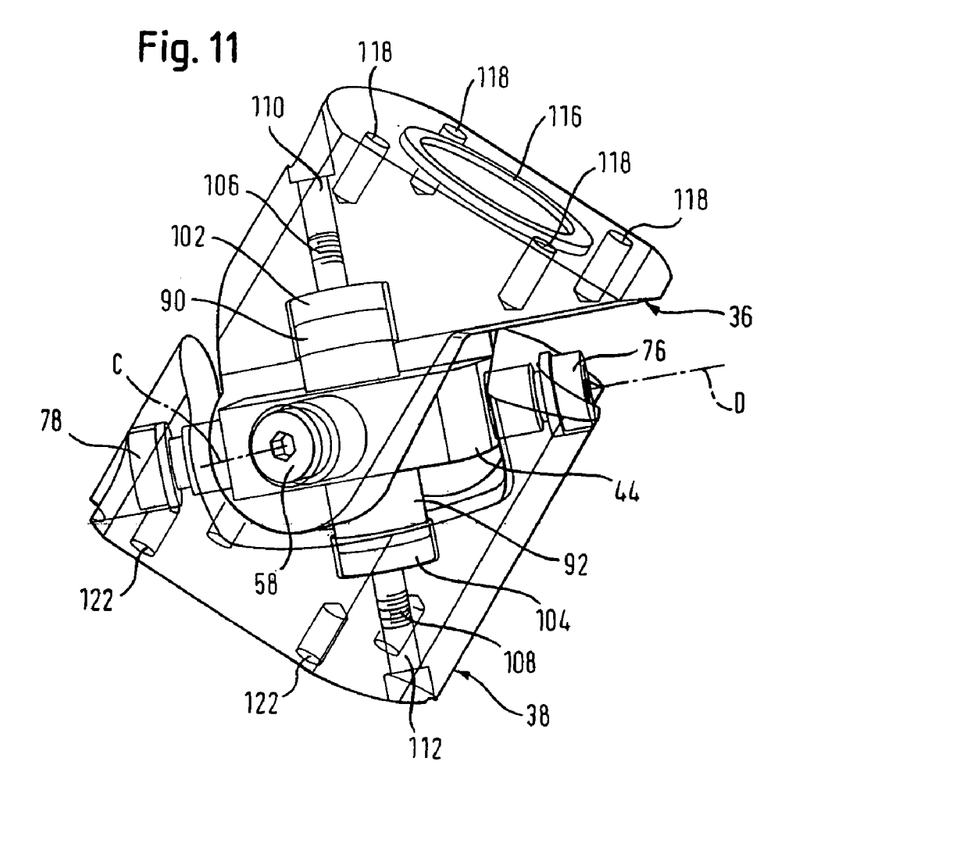

FIG. 8 shows that the shaft-side joint fork 36 comprises a fork base 46 as well as two fork jaws 48 and 50 projecting from the fork base 46. These two fork jaws 48 and 50 encompass a recess 52 inclined at an angle of approximately 80 to the Y-axis shown in FIG. 8.

In recess 52 is received joint element 44. Joint element 44 is Supported rotatably via two bearing bolts 54 and 56 relative to joint fork 36. Each bearing bolt 54 and 56 has a bearing head 58 stayed on a bearing washer 60 on a stepped hole 62 penetrating fork jaws 48 and 50. On both sides of the recess 52 friction bearing bushings 64 and 66 are pressed into the stepped hole 62 such that they are torque tight and stayed via flanges. The bearing bolts 54 and 56 have at their ends outer thread sections 68, 70 projecting into the recess 52. The outer thread sections 68, 70 are fixedly screwed into a corresponding tapped through hole 72 in joint element 44. Between the two outer thread sections 68, 70 a compression disk 74 is disposed at the side ends.

Through this disposition the joint element 44 is swivellable relative to the first joint fork 36 about the first rotational axis C swivelled with respect to the Y-axis. In the same manner, as is evident in FIG. 2, 3 and 4 as well as 10 and 11 in detail, joint element 44 is supported via bearing bolts 76, 78 relative to the treading-side joint fork 38.

It should additionally be pointed out that the individual bearing heads 58 of bearing bolts 54, 56, 76, 78 are received in recesses with corresponding diameters in the joint forks and thus are at least partially sunk into them, such that they at most project minimally beyond a shell surface enveloping the particular joint fork 36 or 38.

It should further be pointed out that the treading-side joint fork 38 also comprises a joint [sic: fork] base 80 as well as two fork jaws 82 and 84, which encompass a recess 86. The recess 86 is also inclined relative to the Y-axis, namely at an angle of approximately 42°.

In the manner of a Cardan joint or universal joint, both joint forks 36, 38 extend with their fork jaws 48, 50, 82, 84 into the particular recess 52 or 86, respectively, of the particular other joint fork 38 or 36, respectively, and consequently encompass the joint element 44 on four opposing sides of the end face.

In the depicted disposition is evident a universal joint 32, which, after installation according to FIG. 1, in the resting position is oriented such that the first rotational axis C in the plane spanned by the X- and Y-axes is inclined at an angle of approximately 6° relative to the Y-axis, in the plane spanned by the Y- and Z-axes at an angle of approximately 82° relative to the Z-axis and in the plane spanned by the X- and Z-axes at an angle of approximately 10° relative to the X-axis, when the prosthetic device is in its relaxed position.

Under these considerations of the prosthetic foot 30 in the relaxed position, an orientation results with respect to the second rotational axis D in which the second rotational axis D in the plane spanned by the X- and Y-axes is inclined at an angle of approximately 23° relative to the X-axis, in the plane spanned by the Y- and Z-axis at an angle of approximately 45° relative to the Y-axis and in the plane spanned by the X- and Z-axis at an angle of approximately 41° relative to the X-axis.

In the installed state depicted in FIG. 1 the two rotational axes C and D in the resting position in the system of coordinates spanned by the X-, Y- and Z-axes accordingly have substantially the same orientation as the rotational axes A and B of the upper ankle joint OSG and the lower ankle joint USG corresponding to the schematic representation of the standard foot according to FIG. 12a to 12h.

The two rotational axes C and D of the universal joint mechanism 32 are moreover also substantially disposed at the same height above ground as is the case in the standard foot depicted in FIG. 12a to 12h, that is in the region of its ankle. Consequently, the same rotational movements can be carried out with the axial configuration as is the case with the upper and lower ankle joint of a natural human foot 16 according to FIG. 12a to 12h and as was explained above with reference to FIG. 13a and 13b.

The rotational axes C and D and the corresponding capability of relative rotational movement of joint forks 36 and 38 as well as joint element 44 were explained above. In the following the manner will be described in which such movements are damped or restricted.

For this purpose damping elements 90, 92 are provided. The damping elements 90, 92 are formed of hollow cylindrical rubber bodies, in particular polyurethane bodies, which press onto the side faces 94, 96 of joint element 44. The damping elements 90, 92 are received in corresponding receiving openings 98, 100. On their side remote from joint element 44 the damping elements 90, 92 are in contact on pressure disks 102, 104 guided in the receiving openings 98, 100. The pressure disks 102, 104 can be displaced within the receiving openings 98 and 100 under guidance via threaded bolts 106, 108. The threaded bolts 106 and 108 are screwed into adjustment bores 110 and 112 with corresponding inner thread sections and within these are adjustable through external access.

This permits pressing the damping elements 90, 92 via the pressure disks 102, 104 by means of the threaded bolts 106 and 108 more or less strongly onto the side faces 94, 96 of joint element 44 and therewith to restrict its motility, in particular rotatability about the rotational axes C and D more or less strongly. Expressed differently, by screwing the threaded bolts 106 and 108, the particular pressure disk 102 or 104 is pressed more strongly onto the damping element 90, 92 and consequently the particular damping element 90, 92 is pressed more strongly onto the front side 94, 96 of joint element 44, that is, the damping element is advanced. Damping elements 90, 92 engage over an area of such size on the front face 94, 96 that the effective lever arm of the engagement sites with respect to the particular rotational axis C or D is sufficiently long to effect a resistance, as a function of the pressing force of the particular damper element 90, 92, against any displacement from the resting position of joint element 44 about the particular rotational axis C or D.

Figure 6:
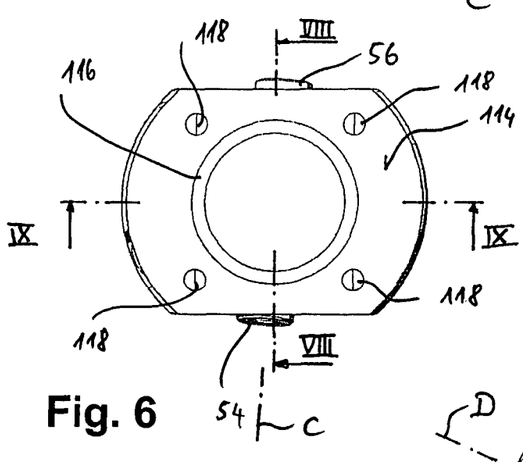
Figure 7:
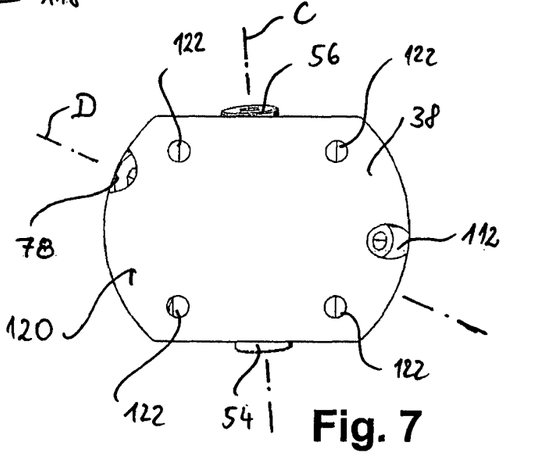

Additionally should be noted that on the upper side 114 of the shaft-side joint fork a receiving ring 116 as well as fastening bores 118 are provided to attach a shaft adapter, for example a pyramid adapter, as shown in FIG. 6. On the underside 120 of the treading-side joint fork 38 are furthermore located four fastening openings 122 to attach the treading attachment 40.

It should further be remarked that the fork bases 46 and 80 of joint forks 36 and 38 are so implemented that they give the particular other joint fork 38 or 36 sufficient play for movements corresponding to the movement capabilities of inversion, eversion, plantar flexion, dorsiflexion, pronation and supination within the scope of the natural movement of a human foot without the two joint forks directly abutting one another. Through the invention such mutual direct contact of the two joint forks 36 and 38 is intended to be prevented to the greatest possible extent. Rather—as stated above—according to the invention a limitation of the movement is to be attained through the damping elements 90, 92.

Due to the invented prosthetic device 30, provided with the above extensively described universal joint mechanism 32 according to the orientation depicted in FIG. 1, such that rotational axes C and D, corresponding to the natural orientation of a healthy foot, are substantially congruent with the orientation of the rotational axes of the upper ankle joint or of the lower ankle joint, a dynamic sequence modeling of a natural gait pattern can be attained in ideal manner.

This means that the above phases and relative movements, described for a better understanding with reference to FIG. 13a and 13b, passed through during walking are nearly identically modeled through the invented prosthetic device. Consequently, with the invented prosthetic device 30 according to FIG. 13a, when placing the device down up to a middle stance phase, an inner rotation can be achieved of the shaft 34 (arrow 18) and the shaft-side joint fork 36 fixedly connected with the shaft with the simultaneous eversion (arrow 20) of the treading attachment 40. During a subsequent roll-off and push-off from the front end, remote from the universal joint, of the treading attachment 40, an outer rotation takes place with the invented prosthetic device 30 according to FIG. 13b (arrow 22) of the shaft and 34 and the shaft-side joint fork 36, fixedly coupled thereto, and the synchronous inversion of the treading attachment 40 corresponding to arrow 24.

Figure 14:
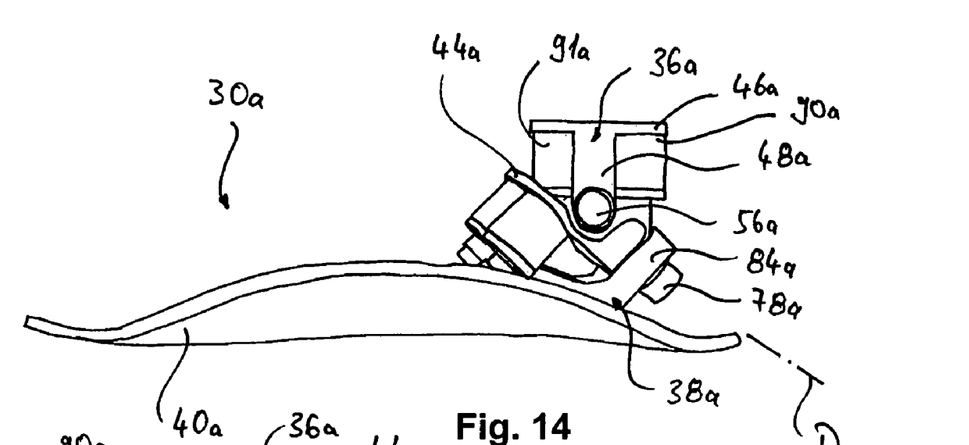
Figure 15:
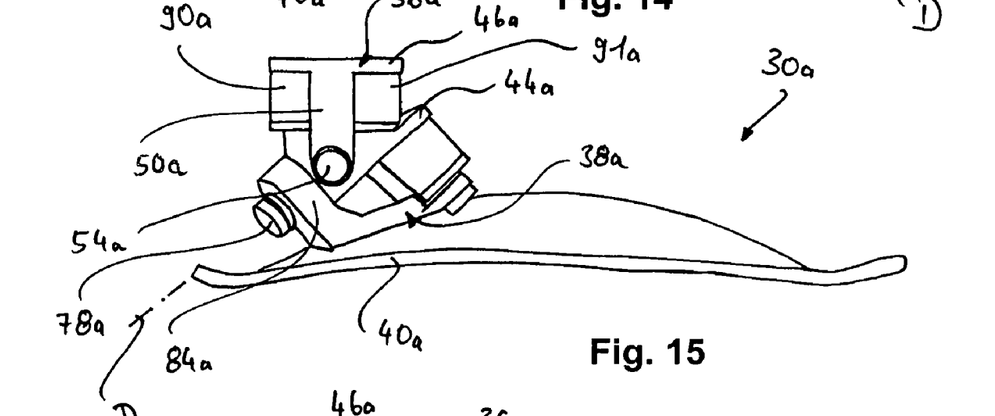
Figure 16:
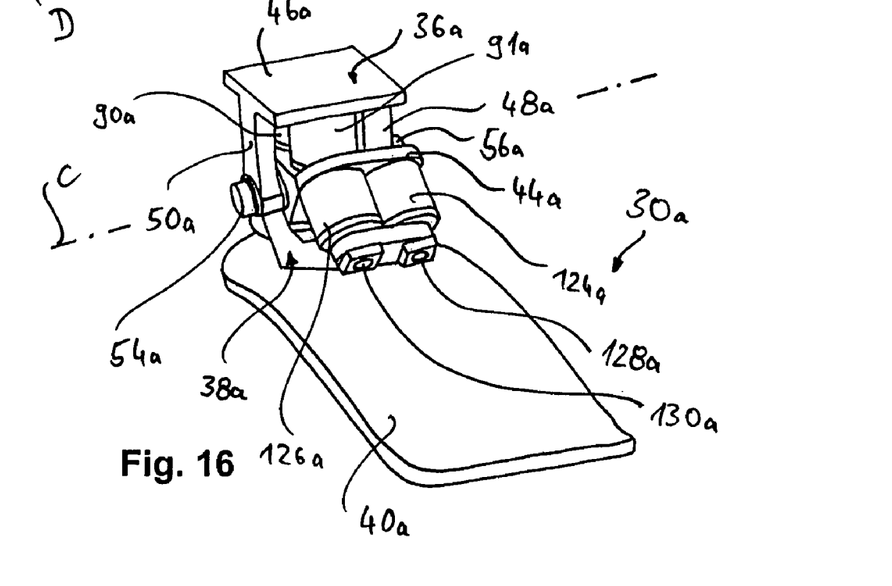

FIG. 14 to 16 show a second embodiment example of the invented prosthetic device. While the structure of this second embodiment example differs slightly from the first embodiment example according to FIG. 1 to 11, however its function is substantially the same. To avoid repetitions therefore for identical or identically functioning components, reference numbers identically to those of the first embodiment according to FIG. 1 to 11 are used, however with the lower case "a" affixed.

In this embodiment the shaft-side joint part is also implemented as a joint fork 36a. It comprises two fork jaws 48a and 50a connected with the plate-form base 46a. In each fork jaw 48a and 50a are disposed bearing bolts 54a and 56a coupled with joint element 44a such that joint element 44a is swivellable relative to fork jaws 48a and 50a. Between joint element 44a and base 46a are disposed damping elements 90a and 91a. Each of the damping elements has the form of a circular cylinder and dampens a swivel movement of joint element 44a relative to joint fork 36a about the first rotational axis C. To this extent the structure of the second embodiment example according to FIG. 14 to 15 substantially agrees with the structure of the first embodiment example according to FIG. 1 to 11.

However, the second embodiment example according to FIG. 14 to 16 differs from the first embodiment example with respect to the geometry of the second joint part 38a and the coupling of the second joint part 38a with joint element 44a.

The second joint part 38a is not similarly formed in the shape of a fork as is the first joint part 36a. Rather, the second joint part 38a comprises only one joint flank 84a in which a bearing bolt 78a is located. The bearing bolt 78a penetrates the joint flank 84a and is so coupled with joint element 44a that it is rotatable about the rotational axis D relative to the second joint part 38a. However, no second bearing bolt is associated with this second rotational axis D as is the case in the first embodiment example, but rather the side, remote from the bearing bolt 78a, of joint element 44a is coupled across two damping elements 124a and 126a with the second joint part 38a.

The damping element 124a is received via a fastening bolt 128a, which penetrates joint part 38a and is anchored in joint element 44a, between joint part 38a and joint element 44a. Similarly, the damping element 126a is received via a fastening bolt 130a, which penetrates joint part 38a and is anchored in joint element 44a, between joint part 38a and joint element 44a. With a relative rotation of joint element 44a relative to joint part 38a about rotational axis D, one of the damping elements 124a and 126a is compressed due to the relative tilt of joint element 44a toward joint part 38a.

The configuration according to FIG. 14 to 16 is of lighter weight compared to the first embodiment according to FIG. 1 to 11 and also requires less structural space. This allows disposing the universal joint arrangement at a relatively lower height over a treading surface than is possible in the embodiment according to FIG. 1 to 11. In individual cases it may be required during the patient fitting to provide the universal joint mechanism of such low height, and the axes realized therein, over a treading surface in order to achieve a physiological gait pattern.

However, the prosthesis 30a according to FIG. 14 to 15 exhibits for the remainder the same advantageous properties as described above in detail in view of the first embodiment according to FIG. 1 to 11.

Thereby that with the invented device a nearly identical modeling of the natural gait pattern is possible, the gait of a patient wearing the invented prosthetic device is largely adapted to the natural gait pattern, such that a symmetric gait results and thereby unnatural loading of individual parts of the movement apparatus, in particular of the joints of the healthy leg, the hip as well as the lumbar region of the vertebral spine, are prevented.

The invention claimed is:

1. A foot prosthesis for fitting leg amputees comprising a universal joint mechanism, which couples a vertical shaft with a treading body having a horizontal bottom surface orthogonal to the vertical shaft, through an articulation, wherein the universal joint mechanism comprises a joint element, which is supported rotatably about a first rotational axis (C) and a second rotational axis (D) deviating therefrom,     wherein the universal joint mechanism comprises a shaft-side joint part coupleable with the shaft and a treading body-side joint part coupled via the joint element in an articulation with the shaft-side joint part, wherein the shaft-side joint part is swivellable about the first rotational axis (C) and the treading body-side joint part about the second rotational axis (D) relative to the joint element, and wherein the swivel movements of shaft-side and treading body-side joint part relative to the joint element are carried out against the resistance of at least one elastically deformable damping element,     wherein one damping element is disposed between the joint element and one joint part and a further damping element is provided between the joint element and the other joint part, and     wherein the first rotational axis (C) in a spatial system of coordinates defined by fixed points of the human foot, according to which the orientation of the treading body, after it has been attached to the treading body-side joint part, is determined in a resting position,     in a plane spanned by X- and Z-axes is inclined at an angle of $-10°$ to $30°$ relative to X-axis,     in a plane spanned by Y- and Z-axes is inclined at an angle of $60°$ to $100°$ relative to Z-axis,     and in a plane spanned by X- and Y-axes is inclined at an angle of $-10°$ to $20°$ relative to Y-axis,     wherein when in a relaxed resting position an X-Y plane is defined by the vertical shaft and the horizontal bottom surface and a direction of the X-axis by a longitudinal extent of the horizontal bottom surface, the Y-axis is directed orthogonal and laterally with respect to the X-axis and the Z-axis is orthogonal to the X-axis and the Y-axis, and the Y-axis extends in the lateral direction.

2. A foot prosthesis for fitting leg amputees comprising a universal joint mechanism, which couples a vertical shaft with a treading body having a horizontal bottom surface orthogonal to the vertical shaft, through an articulation, wherein the universal joint mechanism comprises a joint element, which is supported rotatably about a first rotational axis (C) and a second rotational axis (D) deviating therefrom,     wherein the universal joint mechanism comprises a shaft-side joint part coupleable with the shaft and a treading body-side joint part coupled via the joint element in an articulation with the shaft-side joint part, wherein the shaft-side joint part is swivellable about the first rotational axis (C) and the treading body-side joint part about the second rotational axis (D) relative to the joint element, and wherein the swivel movements of shaft-side and treading body-side joint part relative to the joint element are carried out against the resistance of at least one elastically deformable damping element,     wherein one damping element is disposed between the joint element and one joint part and a further damping element is provided between the joint element and the other joint part, and     wherein the second rotational axis (D) in a spatial system of coordinates defined by fixed points of the human foot, according to which the orientation of the treading body, after it has been attached to the treading body-side joint part, is determined in a resting position,     in a plane spanned by X. and Z-axes is inclined at an angle of $-15°$ to $60°$ relative to X-axis,     in a plane spanned by Y- and Z-axes is inclined at an angle of $30°$ to $60°$ relative to Y-axis, and     in a plane spanned by X- and Y-axes is inclined at an angle of $0°$ to $40°$ relative to X-axis,     wherein when in a relaxed resting position an X-Y plane is defined by the vertical shaft and the horizontal bottom surface and a direction of the X-axis by a longitudinal extent of the horizontal bottom surface, the Y-axis is directed orthogonal and laterally with respect to the X-axis and the Z-axis is orthogonal to the X-axis and the Y-axis, and the Y-axis extends in the lateral direction.

\* \* \* \* \*

UNITED STATES PATENT AND TRADEMARK OFFICE
CERTIFICATE OF CORRECTION

PATENT NO.         : 7,862,621 B2                                   Page 1 of 1
APPLICATION NO.    : 11/659169
DATED              : January 4, 2011
INVENTOR(S)        : Ralf Kloos et al.

It is certified that error appears in the above-identified patent and that said Letters Patent is hereby corrected as shown below:

Title Page
        In Item (73) delete Assignee "Fraunhofer-Gesellschaft zur Forderung der Angewandten Forschung E.V."

It should read
    -- Bauerfeind AG --.

Signed and Sealed this
Fourth Day of June, 2013

Teresa Stanek Rea
*Acting Director of the United States Patent and Trademark Office*